United States Patent [19]

Satzinger et al.

[11] Patent Number: 4,587,263
[45] Date of Patent: May 6, 1986

[54] CYCLOALIPHATIC AMINOSULFONIC ACID DERIVATIVES

[75] Inventors: Gerhard Satzinger, Denzlingen; Johannes Hartenstein, Stegen-Wittental; Edgar Fritschi, St. Peter; Wolf-Dieter Vigelius, Denzlingen, all of Fed. Rep. of Germany

[73] Assignee: Warner-Lambert Company, Morris Plains, N.J.

[21] Appl. No.: 634,839

[22] Filed: Jul. 26, 1984

[30] Foreign Application Priority Data

Jul. 29, 1983 [DE] Fed. Rep. of Germany ....... 3327318

[51] Int. Cl.$^4$ .................. A61K 31/185; C07C 143/21
[52] U.S. Cl. .................................... 514/553; 260/503; 558/29; 558/48
[58] Field of Search .......................... 260/503; 514/553

[56] References Cited

PUBLICATIONS

Najer et al., Bull. Soc. Chim. Fr., 1965, pp. 204–208.
Hackenberger, Pharmazie, 34, 494, (1979).

*Primary Examiner*—Nicky Chan
*Attorney, Agent, or Firm*—Ronald A. Daignault

[57] ABSTRACT

New aminosulfonic acids of the general formula I

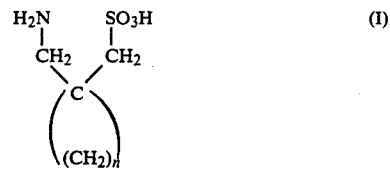

wherein n represents the figures 4, 5, or 6, prepared according to previously known processes and characterized by very good tolerance and valuable cardiovascular properties, serve for the therapy of dysrhythmia and are superior to procaine.

6 Claims, No Drawings

CYCLOALIPHATIC AMINOSULFONIC ACID DERIVATIVES

BACKGROUND AND FIELD OF INVENTION

Cycloaliphatic aminosulfonic acid derivatives have been shown to have valuable cardiovascular properties with very good tolerance and are particularly well suited for the therapy of undesired generation and conduction of stimuli in the tissue which, for example, occur with dysrhythmia.

The preparation of choice for the treatment of the disorders mentioned is still procainamide which is the prototype for directly acting antiarrhythmic pharmaceuticals. Procainamide has the severe disadvantage that its use reduces all base functions of the heart. The necessary high dosage and the small therapeutic range as well as the markedly undesired accompanying phenomena such as the danger of collapse and shock, tachycardia, thrombopenia, agranulocytosis, and gastrointestinal and allergic phenomena make the search for chemically new substances, which do not show the disadvantages mentioned, absolutely necessary, see *Pharmazie.* 34, p. 494–498 (1979).

SUMMARY OF THE INVENTION

Accordingly, the subject of the present invention are new cycloaliphatic aminosulfonic acid derivatives of the general formula I

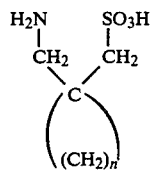

wherein n represents the FIGS. 4, 5, or 6, pharmaceutical preparations therefor and a method for treating cardiovascular diseases therewith.

DETAILED DESCRIPTION

The compounds of the general formula I can be prepared by converting a compound of the general formula II

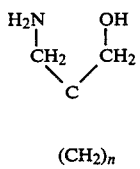

wherein n has the aforementioned meaning in a previously known manner into a reactive ester and reacting it with a soluble inorganic sulphite, in particular an alkali sulphite.

The compounds of the general formula II are known (*Bull. Soc. Chim. Fr.* 1965, p. 204–208) or can be prepared according to known methods.

Reactive esters suited for use are those of strong inorganic or organic acids. Halides and sulphuric acid esters are especially suited. Sulphuric acid semiesters of the general formula II

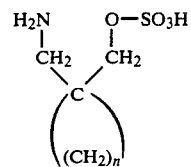

wherein n has the aforementioned meaning are particularly preferred.

The compounds III are also known compounds (*Bull. Soc. Chim. France* loc. cit).

The conversion of the compounds of the general formula III into aminosulfonic acids of the general formula I is effected by substituting the radical —O—SO$_3$H, which is to be split off, by sulphite. It is advisable to carry out the reaction in such a way that the compund III is reacted with an alkali sulphite, such as sodium or ammonium sulphite, under heat and in a suitable solvent. The sulphuric acid semiesters of the general formula III are preferably heated in water with an equivalent or excessive quantity of sodium sulphite to temperatures of 100°–180° C., preferably 160° C. in the autoclave. The reaction of other reactive esters, such as halides, is carried out analogously.

Another subject of the present invention are drugs, i.e., pharmaceutical preparations, with cardiovascular properties which, in addition to the usual pharmacologically acceptable carriers such as filling material and excipients, contain at least one compound of the general formula I.

Subject of the invention is also the use of compounds of the general formula I for treating cardiovascular diseases.

Because of the good tolerance of the compounds and depending on the degree of severity of the disease, the oral or parenteral single dose for man will approximately be within the range of 20–250 mg.

The compounds of the general formula I according to the invention allow oral or parenteral administration in liquid or solid form. The injection solution of choice is water in particular which contains the conventional additives for injection solutions such as stabilizers, solubilization agents, or buffers.

Such additives include, for example, tartrate and citrate buffers, ethanol, complex formers (such as ethylenediaminetetraacetic acid and its nontoxic salts) as well as high molecular weight polymers (such as liquid polyethylene oxide) for viscosity regulation. Examples for solid carrier substances include starch, lactose, mannitol, methyl cellulose, talc, highly dispersed silicic acids, high molecular weight fatty acids (such as stearic acid), gelatin, agar-agar, calcium phosphate, magnesium stearate, animal and vegetable fats, and solid high molecular weight polymers (such as polyethylene glycol). Compositions suitable for oral administration can, if desired, contain additional flavoring and/or sweetening agents.

The following example is given for the purpose of illustrating the invention:

EXAMPLE

1-Aminomethylcyclohexylmethanesulfonic acid 33.4 g (150 mmol) 1-aminomethylcyclohexyl methyl hydrogen sulfate and 37.8 g (300 mmol) sodium sulphite are heated to 160° C. for 6 hours in 150 ml water in the autoclave. After cooling, the crystal slurry is vigorously sucked off, subsequently washed with a small amount of ice water and recrystallized from water. There is obtained 1-aminomethylcyclohexylmethanesulfonic acid in form of colorless needles which melt in a range of 390° and 410° C.

Starting from 1-aminomethylcyclopentylmethyl hydrogen sulfate or 1-aminomethylcycloheptylmethyl hydrogen sulfate, 1-aminomethylcyclopentylmethanesulfonic acid and 1-aminomethylcycloheptylmethanesulfonic acid are obtained analogously.

PHARMACOLOGICAL COMPARATIVE STUDY

1-Aminomethylcyclohexylmethanesulfonic acid/procainamide

Therapeutic action in CaCl$_2$-induced arrhythmia on rats (Arrhythmia resulting from extracellular disturbance in electrolyte).

Method: Arrhythmia is induced in anesthetized rats by intravenous infusion of calcium chloride solution. It lasts for a certain period after terminating the infusion (modified acc. to Malinow, M. R. et al., *Arch. int. Pharmacodyn.*, 102, 266 (1955)). This arrhythmic phase is cancelled by the prophylactic administration of antiarrhythmic agents. The effects of the substance (I) according to the invention are compared with those of procainamide.

| Substance | Arrhythmogenic quantity CaCl$_2$ solution in mg/kg | Substance dose for the cancellation of arrhythmia (mg/kg IV)* | LD50 (IG)* mg/kg (mouse) |
|---|---|---|---|
| I (n = 5) | 278 ± 35 | 5 | >1600 |
| Procainamide | 193 ± 27 | 20 | 1200 |
| Control (NaCl) | 59 ± 10 | — | — |

*IV = intravenous;
*IG = intragastric.

As regards tolerance and potency, the compounds according to the invention are superior to the known antiarrhythmic, procainamide.

We claim:

1. An aminosulfonic acid of the general formula I

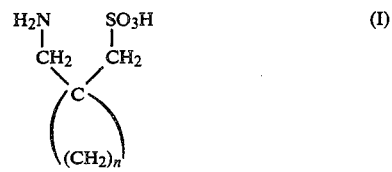

wherein n is 4, 5, or 6.

2. 1-Aminomethylcyclohexylmethanesulfonic acid.

3. A method for treating cardiovascular diseases comprising administering to a host suffering therefrom an effective amount of a compound according to claim 1 in unit dosage form.

4. The method of claim 3 wherein an effective amount of 1-aminomethylcyclohexylmethanesulfonic is used in unit dosage form.

5. A pharmaceutical preparation for treating cardiovascular diseases comprising an effective amount of a compound according to claim 1 together with a pharmacologically acceptable carrier.

6. A preparation according to claim 5 containing an effective amount of 1-aminomethylcyclohexylmethanesulfonic acid.

* * * * *